Oct. 19, 1971 R. H. McCOLLEY Plant Pat. 3,081
PHILODENDRON PLANT
Filed March 10, 1969
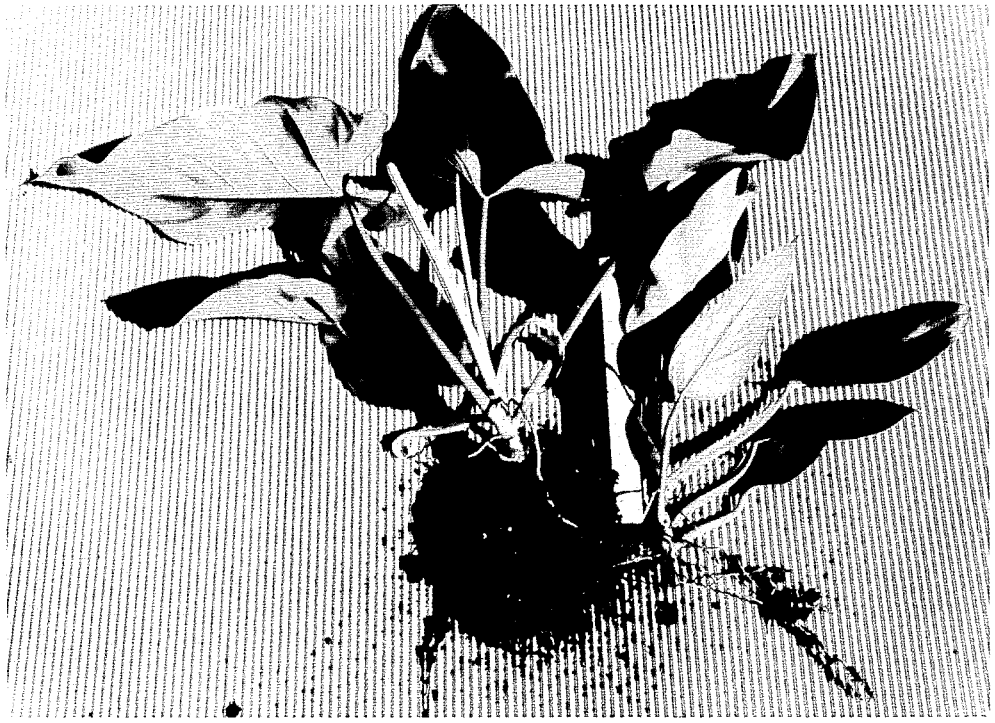
Inventor:
R. H. McCOLLEY
Robb & Robb
attorneys United States Patent Office Plant Pat. 3,081
Patented Oct. 19, 1971

3,081
PHILODENDRON PLANT

Robert H. McColley, Orlando, Fla., assignor to
Yoder Bros., Inc., Barberton, Ohio Filed Mar. 10, 1969, Ser. No. 805,910
Int. Cl. A01h 5/00
U.S. Cl. Plt.—88 1 Claim My present invention comprises a new and distinct variety of philodendron plant which was the result of crossing the unnamed seedling variety which had also been bred and selected by me from a self of philodendron variety Burgundy, and another parent from the species *Philodendron wendlandii.*

The object of my invention has been to produce an improved variety of philodendron which is important for a number of outstanding characteristics, among them its compact upright habit of growth, durable firm texture of leaf with medium strong petioles with prominent lenticels, with perhaps the most important improvement being the very great resistance to "shotgun fungus," a designation which was adopted in the trade before it was discovered to be a physiological rather than a biological reaction to certain environmental conditions.

My present new variety is essentially the result of an extensive hybridizing program which has been carried on for many years in my greenhouses in Orlando, Fla., and involves the selection of different varieties having improved characteristics in my judgment and the result of crossings made by me with careful selection and to produce the new varieties of which the instant seedling is an example.

One of the characteristics of course of the philodendron in general is that it does not usually flower and no flowers in the instant variety have ever been observed by me and philodendrons in general, if they flower, do so only in a sparse manner. The development of flowers would require ideal environmental conditions from fully matured plants in high humid temperatures in the 65° to 75° F. range.

The result of the instant hybridization of my new variety herein mentioned and described, has been to produce the same with leaf, stem and petiole color characteristics ranging from the top surface of the leaves at 7.5GY4/4 in the mature plant to a 5GY5/6 top surface in an immature plant.

The philodendron of my new variety is a climber and where the plants produce eight leaves or over, will require a normal staking with a medium rate of growth.

Under normal greenhouse conditions, a young plant may be developed in 3½ months from a tip cutting. A mature plant will require 6½ months to grow from the same type of cutting.

As grown in the greenhouse in Orlando, Fla., the plants will attain a height of 18 inches with a spread of 24 inches, if an average plan of 5 leaves, propagated from tip cuttings, is availed of for such production.

The variety is vigorous, compact and non-branching.

My new variety may be distinguished from the male parent by noting that my new variety is a compact climber in contrast to the self header and rosette type of growth of said male parent with the leaf shape in my new variety being lanceolate-ovate and of durable, firm texture in contrast to the oblanceolate and soft texture of the male parent.

Another distinguishing feature of my new variety is the fact that the petioles are medium strong with prominent lenticels on the upper and lower surfaces, often extending under the surface of the midrib in contrast to the male parent in which petioles are very short with no lenticels observable.

While the female parent has some resistance to "shotgun fungus," the instant variety is very resistant to such leaf spotting and while the petioles of my instant variety are medium green, the red petioles of the female parent and lack of lenticels distinguish the same therefrom.

Since the philodendron industry standard is known to be the so-called "Emerald Queen," comparison is made with that particular variety and also with other varieties known as *P. brenessi, P. cordatum* (true species) and *P. ficutissimum.*

A new variety is distinguished from Emerald Queen by certain unique characteristics including:

(1) The Sagittate—cordate basal leaf lobes are considerably more extended.

(2) The very prominent and profuse purple colored lenticels on the leaf sheaf, upper and lower surfaces of leaf petioles providing unique and interesting markings which add to the appearance of the plant. Emerald Queen has few if any and they are obscure.

Further, the leaf sheaf is quite prominent due to its length which is often twice the size of Emerald Queen's with profuse and brightly colored lenticels.

Further, the instant variety has a thick, more leathery leaf which contributes to its keeping quality in the home.

*P. cordatum* has a very thin leaf and is not adapted for long home life.

The leaves of *P. ficutissimum* crack easily in shipping and in contrast to those of my new variety.

Additionally, the length of the leaf petiole of my new variety is approximately two-thirds the length of the leaf providing a more compact appearance. Emerald Queen is about four-fifth the length, *P. brenessi* has a leaf petiole approximately equal the length of the leaf, and *P. cordatum* has leaf petioles approximately 4" to 6" longer than the leaf.

My new variety has stems which are almost twice the caliper of Emerald Queen.

Additionally, as previously stated my new variety has very high resistance to the disease bacterial soft rot which Florida and Gulf Coast foliage producers find very difficult to overcome. Emerald Queen and *P. brenessi* are only slightly resistant. *P. ficutissimum* and *P. cordatum* are extremely susceptible to the soft rot.

Further detailed comparisons might be made but it is believed clear from the foregoing that my new variety is indeed distinct from those varieties referred to herein by being well known in the trade.

My new variety has been asexually reproduced by tip cuttings in the vicinity of Orlando, Fla., where observations were made upon which the description herein set forth subsequently in detail is based.

My new variety has been found to retain its distinctive characteristics through successive asexual reproduction.

The accompanying drawing forming a part hereof, shows a typical plant of my new variety, the color being as nearly representative of the actual color of the plant as is possible in such an illustration.

The color references are made based upon comparison with those in the Munsell Book of Color—1963 edition, with observations being recorded by daylight illumination under clear vinyl of not more than 30% light reduction (Bailey, L. H. and Bailey, E. Z., Hortus Second 1949, page 10).

*Description*

Parentage: Seedling.

*Male parent.*—Unnamed seedling of the species *Philodendron wendlandii.*

*Female parent.*—Unnamed seedling, Philodendron—variety Burgundy.

Classification: Botanic—*Philodendron wendlandii.*

Leaf form characteristics:

*Shape.*—Immature leaf—Lanceolate. Mature leaf—Ovate.

*Tip.*—Acute.

*Base.*—Auriculate.

*Leaf attachment.*—Stalked.

*Leaf arrangement.*—Alternate.

*Margin.*—Entire.

*Displacement.*—Smooth.

*Veination.*—Pinnate.

*Lenticels.*—Prominent on upper and lower surfaces of petioles often extended onto under surface of midrib. Color of lenticels—5R 2/4.

*Leaf sheathing.*—Prominent on all petioles except those capable of producing flowering buds.

| | Mature | Immature |
|---|---|---|
| Leaf size characteristics: | | |
| Leaf itself: | | |
| (a) Width, inches: | | |
| (1) Widest point | 7–9 | 4–5 |
| (2) 1″ from tip | 4–6 | 2–3 |
| (b) Length, inches | 15–18 | 6–8 |
| Leaf petiole: | | |
| (a) Length, inches | 10–14 | 5–7 |
| (b) Width, inches | ⅜–½ | ⅜–½ |
| Leaf, stem and petiole color characteristics: | | |
| Leaf itself: | | |
| (a) Top surface | 7.5 GY 4/4 | 5 GY 5/6 |
| (b) Bottom | 2.5 GY 4/3 | 2.5 GY 5/5 |
| Leaf ribs and veins: | | |
| (a) Top | 5 GY 5/6 | 5 GY 5/6 |
| (b) Bottom | 2.5 GY 5/4 | 2.5 GY 5/5 |
| Stem and petiole; (a) Lenticels | 5 GY 5/6<br>5R 2/4 | 5 GY 5/6<br>5R 2/4 |

I claim:

1. A new and distinct variety of philodendron plant substantially as herein disclosed, characterized as to novelty by its robust, compact, upright habit, the firm texture of its leaves, the strong petioles with prominent lenticels, long lastingness in the greenhouse and under home conditions, together with its outstanding resistance to "shotgun fungus."

References Cited

Exotica 3, A. B. Graft, 1963, Roehs Co., Rutherford, N.J., pp. 207, 216, 217, 220, 1684 and 1685 relied on.

ROBERT E. BAGWILL, Primary Examiner